United States Patent [19]

Tien et al.

[11] Patent Number: 5,567,823
[45] Date of Patent: Oct. 22, 1996

[54] PROCESS FOR THE PREPARATION OF AN HIV PROTEASE INHIBITING COMPOUND

[75] Inventors: Jien-Heh J. Tien, Libertyville, Ill.;
Jerome A. Menzia, Kenosha, Wis.;
Arthur J. Cooper, Lake Villa, Ill.

[73] Assignee: Abbott Laboratories, Abbott Park, Ill.

[21] Appl. No.: 469,965

[22] Filed: Jun. 6, 1995

[51] Int. Cl.$^6$ ................................................. C07D 417/12
[52] U.S. Cl. ................................................. 548/204
[58] Field of Search ................................................. 548/204

[56] References Cited

U.S. PATENT DOCUMENTS 5,142,056   8/1992   Kempe ................................. 546/265

FOREIGN PATENT DOCUMENTS

WO94/14436   7/1994   WIPO.

OTHER PUBLICATIONS

Pennington, Peptide Synthesis Protocols, Human Press pp. 1–10 (1994).
Prasad, et al., Int. J. Peptide Protein Res. 25 408 (1985).
Benoiton, et al., Int. J. Peptide Protein Res. 42 278 (1993).

*Primary Examiner*—Robert Gerstl
*Attorney, Agent, or Firm*—Steven R. Crowley

[57] ABSTRACT

Processes are disclosed for the preparation of (2S,3S,5S)-5-(N-(N-((N-Methyl-N-((2-isopropyl-4-thiazolyl)methyl)amino)carbonyl)-L-valinyl) amino)-2-(N-((5-thiazolyl)methoxycarbonyl)amino)-1,6-diphenyl-3-hydroxyhexane or an acid addition salt thereof and (2S,3S,5S)-5-(N-(N-((N-Methyl-N-((2-isopropyl-4-thiazolyl) methyl)amino)carbonyl)-D-valinyl)amino)-2-(N-((5-thiazolyl) methoxycarbonyl)amino)-1,6-diphenyl-3-hydroxyhexane or an acid addition salt thereof.

8 Claims, No Drawings

PROCESS FOR THE PREPARATION OF AN HIV PROTEASE INHIBITING COMPOUND

TECHNICAL FIELD

The present invention relates to a process for the preparation of (2S,3S,5S)-5-(N-(N-((N-Methyl-N-((2-isopropyl-4-thiazolyl)methyl)-amino)carbonyl)valinyl)amino)-2-(N-((5-thiazolyl)methoxycarbonyl)-amino)-1,6-diphenyl-3-hydroxyhexane.

BACKGROUND OF THE INVENTION

It has recently been determined that HIV protease inhibiting compounds are useful for inhibiting HIV protease in vitro and in vivo and are also useful for inhibiting an HIV (human immunodeficiency virus) infection.

It has also recently been determined that compounds of the formula I:

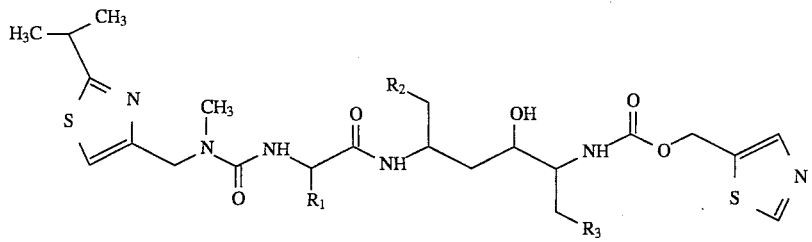

wherein $R_1$ is lower alkyl and $R_2$ and $R_3$ are phenyl are particularly useful as inhibitors of HIV-1 and HIV-2 protease and are useful for inhibiting HIV protease in vitro and in vivo and are also useful to inhibit HIV infections.

In particular, the compound of formula II, has been found to be especially effective as an inhibitor of HIV-1 and HIV-2 protease.

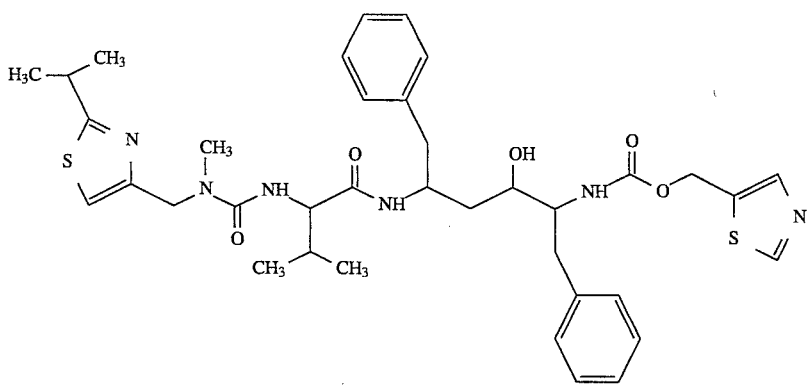

The most preferred compounds of formula II are (2S,3S,5S)-5-(N-(N-((N-Methyl-N-((2-isopropyl-4-thiazolyl)methyl)amino)carbonyl)-L-valinyl)amino)-2-(N-( (5-thiazolyl)methoxycarbonyl)amino)- 1,6-diphenyl-3-hydroxyhexane (compound III) or an acid addition salt thereof and (2S,3S,5S)-5-(N-(N-((N-Methyl-N-((2-isopropyl-4-thiazolyl)methyl)amino)carbonyl)-D-valinyl)amino)-2-(N-((5-thiazolyl)methoxycarbonyl)amino )-1,6-diphenyl-3-hydroxyhexane (compound IV) or an acid addition salt thereof.

The preparation of compound III and its use as an inhibitor of HIV protease are disclosed in PCT Patent Application No. WO94/14436, published Jul. 7, 1994, which is incorporated herein by reference. The method disclosed for preparing compound III is shown in Scheme I. This method involves an amide bond forming coupling reaction of intermediates 1 and 2 in the presence of 1-hydroxybenzotriazole and diimide such as dicyclohexylcarbodiimide (DCC) or N-ethyl-N'-dimethylaminopropyl carbodiimide (EDC) and the like. Such a process is not suitable for manufacturing scale production of III or IV because the diimides are toxic, they are sensitizers and they present a variety of other handling and workup problems.

An alternative process is shown in Scheme II. In this process, intermediate 1 is converted to a mixed anhydride (wherein R* is loweralkyl, for example, by reaction with an alkyl chloroformate such as isobutylchloroformate and the like or by reaction with an alkanoyl chloride such as pivaloylchloride and the like). The mixed anhydride is then reacted (without isolation) with intermediate 2. Because of the high reactivity of the intermediate mixed anhydride, this process often leads to unacceptable amounts of undesired side products.

Therefore, there is a continuing need for an improved coupling process for the preparation of III and IV.

SCHEME I

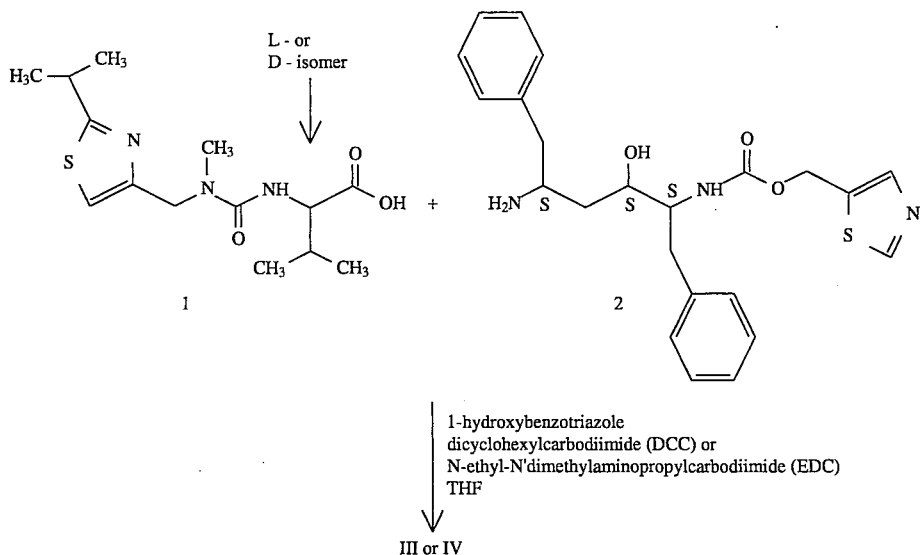

SCHEME II

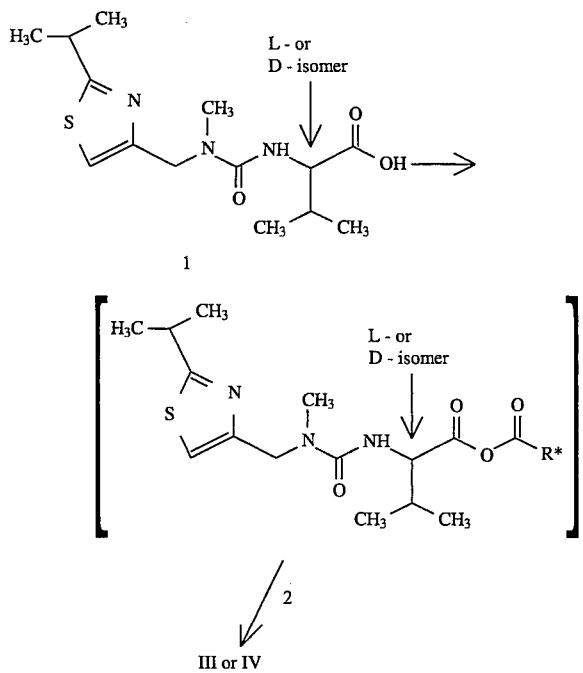

DISCLOSURE OF THE INVENTION

The present invention relates to processes for the preparation of (2S,3S,5S)-5-(N-(N-((N-Methyl-N-((2-isopropyl-4-thiazolyl)methyl)amino)-carbonyl)-L-valinyl)amino)-2-(N-((5-thiazolyl)methoxycarbonyl)amino)-1,6-diphenyl-3-hydroxyhexane (compound III) and (2S,3S,5S)-5-(N-(N-((N-Methyl-N-((2-isopropyl-4-thiazolyl)methyl)amino)carbonyl)-D-valinyl)amino)-2-(N-((5-thiazolyl)methoxycarbonyl)amino)-1,6-diphenyl-3-hydroxyhexane (compound IV). The process is shown in Scheme 3. The process comprises three steps carried out without isolation of the intermediates. The first step comprises formation of an intermediate mixed anhydride derivative 3 (R* is loweralkyl or alkoxy).

In the second step, the mixed anhydride (without isolation) is converted to an intermediate activated ester derivative 4 (R** is selected from the group consisting of succinimid-1-yl, benzotriazol-1-yl, phthalimid-1-yl, 5-norbornene-2,3-dicarboximidyl, quinolin-8-yl, 1,2,3-benzotriazin-4(3H)-on-3-yl, piperidin-1-yl, pentachlorophenyl, 2,4,5-trichlorophenyl, 2-nitrophenyl, 4-nitrophenyl, pentafluorophenyl and the like).

In the third step, the activated ester (without isolation) is reacted with intermediate 2 to give the desired product. This process results in the preparation of highly pure III or IV on a manufacturing scale without complex purification procedures and without exposure to highly toxic or corrosive reagents.

In particular, the process of this invention comprises reacting intermediate 1 with a loweralkylchloroformate (for example, isobutylchloroformate or ethylchloroformate or 2-ethoxy-1-ethoxycarbonyl-1,2-dihydroquinoline (EEDQ) or 2-isobutoxy-2-isobutoxycarbonyl-1,2-dihyroquinoline (IIDQ) and the like) or with a loweralkyl acid chloride (for example, pivaloylchloride and the like) to provide intermediate mixed anhydride 3. This reaction is carried out by reacting compound 1 with from about 0.9 molar equivalent to about 1.0 molar equivalents (based on the amount of compound 1) of the chloroformate or the acid chloride or like reagent in an inert solvent such as ethyl acetate or THF or acetonitrile or toluene and the like at a temperature of from about −20° C. to about 30° C. This reaction is preferably carried out in the presence of from about 1.0 molar equivalents to about 3.0 molar equivalents (based on the amount of compound 1) of an acid scavenger such as N-methylmorpholine or triethylamine or pyridine and the like.

To the resulting solution is added from about 1.0 molar equivalent to about 2.0 molar equivalents (based on the amount of compound 1) of R**OH, maintaining the temperature of the solution at from about −20° C. to about 30° C. to provide the activated ester. To the resulting solution of activated ester is added a solution of intermediate compound 2 in an inert solvent such as ethyl acetate or THF or DMF or acetonitrile or toluene and the like at a temperature of from about −20° C. to about 60° C. The resulting product III or IV can then be purified by recrystallization.

The first step of the process is preferably carried out by reacting intermediate compound 1 with about 1.0 molar equivalents of isobutyl chloroformate in ethyl acetate at about −15° C. in the presence of about 1.5 molar equivalents of N-methylmorpholine.

The second step of the process is preferably carried out by adding about 1.0 molar equivalent of N-hydroxysuccinimide to the solution of the mixed anhydride resulting from step one and maintaining the temperature of the solution at about 0° C.

The third step of the process is preferably carried out by adding to the solution of the activated ester resulting from step two a solution of from about 0.9 to about 1.0 molar equivalent of compound 2 in ethyl acetate at a temperature of about 0° C. This mixture is allowed to warm to about room temperature and is stirred for about 24 hours. The crude product can be purified by recrystallization from heptane/ethyl acetate.

SCHEME III

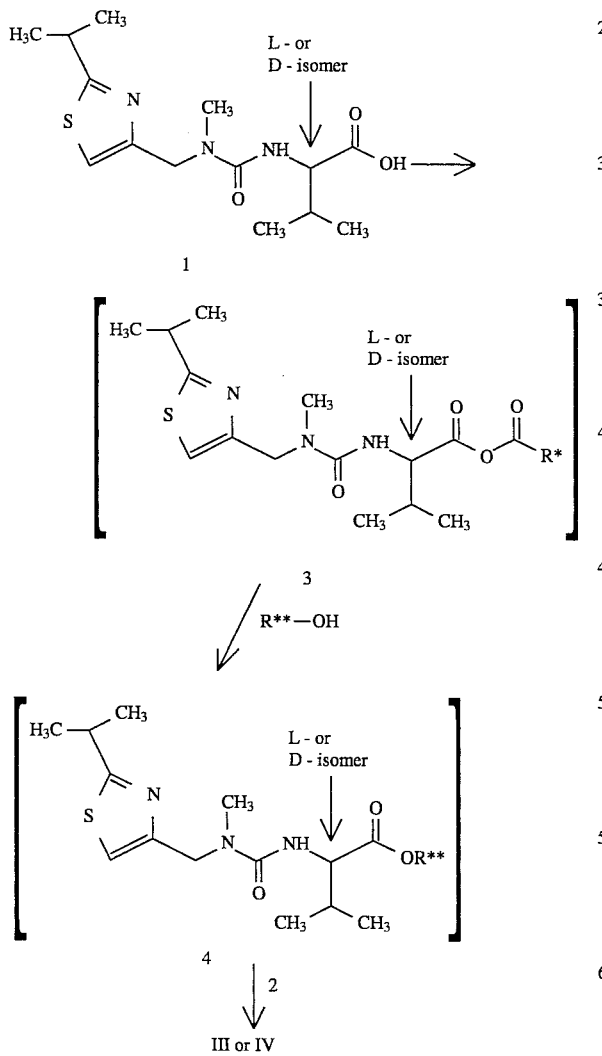

Acid addition salts of the compounds of the invention can be derived from reaction of an amine-containing compound of the invention with an inorganic or organic acid. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate (isethionate), lactate, maleate, malonate, glutarate, malate, mandelate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate.

Examples of acids which may be employed to form acid addition salts include such inorganic acids as hydrochloric acid, sulphuric acid and phosphoric acid and such organic acids as oxalic acid, maleic acid, succinic acid and citric acid, as well as the other acids mentioned above.

The term "loweralkyl" as used herein refers to a straight or branched chain alkyl radical containing from 1 to 6 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "alkoxy" as used herein refers to RO- wherein R is a loweralkyl group.

The term "alkanoyl" as used herein refers to R'C(O)- wherein R' is a loweralkyl group.

As used herein, the terms "S" and "R" configuration are as defined by the IUPAC 1974 Recommendations for section E, Fundamental Stereochemistry, Pure Appl. Chem. (1976) 45, 13 –30.

The following examples will serve to further illustrate the processes of the invention.

EXAMPLE 1

(2S,3S,5S )-5-amino-2-(N-((5-thiazolyl) methoxycarbonyl)amino)-
1,6-diphenyl-3-hydroxyhexane To a 750 gallon glass lined reactor were charged (2S, 3S, 5S)-2-Amino-3-hydroxy-5-(t-butyloxycarbonylamino)-1,6-diphenylhexane—0.5succinic acid salt (75.0 kg, 169 moles), 5-(p-nitrophenyloxycarbonyloxymethyl)thiazole hydrochloride (65.0 kg, 205 moles) and sodium bicarbonate (70.0 kg, 833 moles). Ethyl acetate (826 kg, 918 L) was added and the agitator was started. Tap water (788 kg) was added and the mixture was warmed to 30° C. and stirred for 2.5 hours until all of the solids were dissolved. After settling for 30 minutes, the aqueous layer was separated and discarded. The organic layer was warmed to 60° C. and stirred for 12 hours. The solution was then cooled to 30° C. and 28% ammonia water (9.0 kg, 148 moles) was added. The mixture was stirred for 3 hours at 25°–30° C. The mixture was washed three times with aqueous 10% potassium carbonate solution (903 kg each time). The aqueous layers were drained and discarded after each wash. Concentrated hydrochloric acid (59.0 kg, 600 moles) was added to the ethyl acetate solution and warmed to 50° C. with stirring for 3 hours.

The mixture was then cooled to 40° C. and the resulting precipitate was isolated by centrifugation. Five separate batches of 26 to 51 kg wet weight were obtained and each batch was rinsed with 50 kg of ethyl acetate. The wet solids were combined and charged back into the reactor and slurried in ethyl acetate (723 kg, 803 L). Dilute ammonia water (about 9.4% ammonia, about 190 L) was charged to give a final aqueous pH of about 10.5. The aqueous layer was drained and discarded. The organic layer was washed with 25% sodium chloride solution (513 kg) and the aqueous layer was drained and discarded. The organic layer was filtered into a 300 gallon glass lined reactor and the, solvent was distilled under vacuum at an internal temperature of 40° C. or less. The residue was dissolved in ethyl acetate (576 kg, 640 L) and the solvent was distilled under vacuum until a volume of approximately 290 L was reached.

EXAMPLE 2

(2S,3S,5S )-5-(N-(N-((N-Methyl-N-((2-isopropyl-4-thiazolyl)methyl)amino)carbonyl)-L-valinyl)amino)2-(N-((5-thiazolyl)methoxycarbonyl)amino)-1,6-diphenyl-3-hydroxyhexane To a 750 gallon glass lined reactor was charged N-((N-methyl-N-((2-isopropyl-4-thiazolyl)methyl)amino)carbonyl)-L-valine (57.0 kg, 182 moles) and ethyl acetate (916 kg, 1018 L). The mixture was stirred until everything was in solution and then N-methylmorpholine (28.0 kg, 277 moles) was charged to the reactor and the resulting solution was cooled to −18° C. A solution of isobutyl chloroformate (24.4 kg, 180 moles) in ethyl acetate (101 kg, 112 L) was prepared in a separate reactor. The isobutyl chloroformate solution was charged (over about 50 minutes) into the cold solution of the valine derivative and N-methylmorpholine prepared above, maintaining the temperature at between −18° C. and −14° C. After stirring at −14° C. for about 30 minutes, N-hydroxysuccinimide (21.2 kg, 184 moles) was added to the mixture. After stirring for an additional 30 minutes, the mixture was warmed to about 0° C. and stirred for about one hour.

The resulting solution from Example 1 was cooled to about 0° C and charged slowly into the above solution. A rinse of the 300 gallon reactor with ethyl acetate (50 kg, 56L) was also added. The reaction mixture was warmed to 25 ° C. and was stirred for 24 hours. The reaction mixture was washed twice with 10% potassium carbonate solution (2×711 kg), once with 10% citric acid solution (1025 kg) and once with water (640 kg). The aqueous layers were drained and discarded after each separation. The solvent was distilled under vacuum at an internal temperature of about 50° C. or less. The residue was dissolved in ethyl acetate (576 kg, 640 L) and the solvent was distilled once more. The residue was dissolved in ethyl acetate (500 kg, 556 L) and warmed to about 60° C. until a clear solution was obtained. The solution was filtered into a clean 300 gallon reactor and a rinse of ethyl acetate (77 kg, 86 L) was also filtered into the 300 gallon reactor. Heptane (218 kg, 320 L) was charged to the ethyl acetate solution in the 300 gallon reactor. The mixture was heated to about 80° C. until a clear solution was obtained. The solution was cooled at a rate of less than 25° C. per hour to a final temperature of 22° C. and was stirred for another 12 hours after the product began to crystallize. The thick slurry was centrifuged in four separate loads to isolate the product. Each isolated load was washed with approximately 45 kg of a 2:1 (v/v) solution of ethyl acetate/heptane. The last wash was used to also rinse the reactor. The product was dried in a blender drier under vacuum at 55° C. for about 24 hours to provide 101.9 kg of the desired product.

m.p. 121°–123° C. $^1$H NMR: (CD$_3$OD, 300 MHz) δ 7.78–7.96(m, 1H), 7.85 (s, 1H), 7.07–7.33 (m, 11H), 6.68–6.75 (m, 1H), 6.17–6.28 (m, 1H), 5.22 (s, 2H), 4.47–4.67 (m, 2H), 4.32–4.45 (m, 1H), 3.98–4.10 (m, 2H), 3.72–3.82 (m, 1H), 3.28–3.40 (m,1H), 3.02 (s, 3H), 2.67–2.92 (m, 4H), 1.92–2.08 (m, 1H), 1,56–1.80 (m, 2H), 1.37–1.46 (m, 6H), 0.84–0.96 (m, 6H). $^{13}$C NMR; (CD$_3$OD, 75 MHz) δ 176.0, 169.8, 155.7, 153.7, 152.4, 149.3, 139.3, 139.2, 135.8, 135.2, 126.3, 126.0, 124.9, 124.8, 122.9, 122.8, 111.2, 111.1,66.5, 57.6, 57.5, 54.5, 52.9, 52.8, 45.4, 37.3, 35.7, 34.9, 30.9, 30.0, 27.7, 19.3, 19.2, 15.7, 14.5.

EXAMPLE 3

(2S,3S,5S)-5-(N-(N-((N-Methyl-N-((2-isopropyl-4-thiazolyl)methyl)amino)carbonyl)-D-valinyl)amino)-2-(N-((5-thiazolyl)methoxycarbonyl)amino)-1,6-diphenyl-3-hydroxyhexane The title compound is prepared following the procedure of Example 2 with replacement of N-((N-methyl-N-((2-isopropyl-4-thiazolyl)methyl)amino)carbonyl)-L-valine with N-((N-methyl-N-((2-isopropyl-4-thiazolyl)methyl)amino)carbonyl)-D-valine.

m.p.68°–69° C. $^1$H NMR (DMSO-d$_6$) δ 0.56 (d, J=6Hz, 3H), 0.63 (d, J=6Hz, 3H), 1.28 (d, J=7Hz, 6H), 1.47 (m, 2H), 1.77 (octet, J=6Hz, 1H), 2.5–2.7 (m, 4H), 2.85 (s, 3H), 3.20 (heptet, J=7Hz, 1H), 3.4 (m, 1H), 3.6 (m, 1H),3.90 (dd, J=8, 6Hz, 1H), 3.93 (m, 1H), 4.43 (AA', 2H), 4.65 (d, J=6Hz, 1H), 5.15 (AA', 2H), 6.02 (br d, J=9Hz, 1H), 6.90 (br d, J=9Hz, 1H), 7.1–7.2 (m,11H), 7.70 (br d, J=9Hz, 1H), 7.85 (s, 1H). 9.04 (s, 1H). Mass spectrum: (M+H)$^+$ =721.

EXAMPLE 4

Alternative Preparation of (2S,3S,5S)-5-(N-(N-((N-Methyl-N-((2-isopropyl-4-thiazolyl)methyl)amino)carbonyl)-L-valinyl)amino)-2-(N-((5-thiazolyl)methoxycarbonyl)amino)-1,6-diphenyl-3-hydroxyhexane To a 250 mL 4-neck round bottom flask equipped with a mechanical stirrer, nitrogen atmosphere, 60 mL side arm addition funnel and a thermocouple was charged N-((N-methyl-N-((2-isopropyl-4-thiazolyl)methyl)amino)carbonyl)-L-valine (5.03 g, 16 mmoles) and ethyl acetate (93 mL). The mixture was stirred until all of the solids were dissolved and was then cooled to −15° C. To the cooled solution was added N-methylmorpholine (1.77 ML, 16 mmoles). The mixture was cooled to −18° C. Isobutyl chloroformate (2.08 mL, 16 mmoles) in ethyl acetate (8 mL) was added, maintaining the temperature of the reaction mixture below −14.5° C. After stirring for 1 hour at −17° C., 1-hydroxybenzotriazole (2.46 g, 16 mmoles) was added in one portion. The resulting slurry was warmed to 0° C. and was maintained at or below 0° C. as (2S,3S,5S)-5-amino-2-(N-((5-thiazolyl)methoxycarbonyl)amino)-1,6-diphenyl-3-hydroxyhexane (6.4 g, 15 mmoles) in ethyl acetate (25 mL) was added. The resulting mixture was stirred at 0° C. for 1 hour and then allowed to warm to room temperature and stirred for 15 hours. To the reaction mixture was added 75 mL of 5% aqueous sodium bicarbonate. The organic layer was separated and washed again with 75 mL of 5% aqueous sodium bicarbonate, followed by washing twice with 75 mL of 10% aqueous citric acid each time and, finally, with 75 mL of water. The solvent was removed under vacuum and the residue crystallized from 270 mL of heptane/ethyl acetate 1:1 to provide 9.25 g of the desired product.

EXAMPLE 5

Alternative Preparation of (2S,3S,5S)-5-(N-(N-((N-Methyl-N-((2-isopropyl-4-thiazolyl)methyl)amino)carbonyl)-L-valinyl)amino)-2(N-((5-thiazolyl)methoxycarbonyl)amino)-1,6-diphenyl-3-hydroxyhexane In a three liter flask, N-((N-methyl-N-((2-isopropyl-4-thiazolyl)-methyl)amino)carbonyl)-L-valine (196.6 g, 0.627 moles) and 1-hydroxybenzotriazole (107 g, 0.701 moles) and THF (1.6 L) were mixed. A solution of dicyclohexylcarbodiimide (129.4 g, 0.627 moles) in THF (200 mL) was added in one portion. The resulting mixture was stirred overnight at room temperature.

The reaction mixture was filtered and the filter cake was washed with THF (500 mL). The filtrate was added to a solution of (2S,3S,5S)-5-amino-2-(N-((5-thiazolyl) methoxycarbonyl)amino)-1,6-diphenyl-3-hydroxyhexane (238.9 g, 561 moles) dissolved in THF (3.5 L) at room temperature. After stirring for 4 hours, the THF was evaporated under reduced pressure. The residue was dissolved in methylene chloride (2L) and washed 0.5 M aqueous NaOH (1.25 L) and then with ½ saturated aqueous sodium bicarbonate (1L). The organic solution was then washed with 1% aqueous KH$_2$SO$_4$ (1 L). The resulting mixture was filtered and the phases separated. The organic solution was washed with 1 L of a 1:1 mixture of ½ saturated aqueous sodium chloride and ½ saturated pH 7 aqueous phosphate buffer. The organic solution was then dried over Na$_2$SO$_4$ and the solvent evaporated to give a tan foam.

The crude product was dissolved in methylene chloride (1.1 L) and the solvent evaporated to provide a brittle foam. This foam was dissolved in 1M aqueous HCl (3 L) at 10° C. The resulting insoluble material was filtered and the filter cake was washed with 1M aqueous HCl (100 mL). In a 12 L Morton flask, the filtrate was combined with KH$_2$PO$_4$ (100 g) and methylene chloride (2.2 L). With rapid stirring, the solution was neutralized to pH 6 with 2M aqueous NaOH. The bottom layer was drained and the aqueous layer was extracted with methylene chloride (2×500 mL). The combined organic layers were dried over Na$_2$SO$_4$, diluted with ethyl acetate (1 L) and concentrated to a colorless foam.

The resulting solid was recrystallized by dissolving in hot ethyl acetate (2 L), diluting with hot hexane (1 L), addition of seed crystals, stirring until cool and letting stand at room temperature overnight to provide the desired product as a white solid. m.p. 122° C.

The foregoing is merely illustrative of the invention and is not intended to limit the invention to the disclosed embodiments. Variations and changes which are obvious to one skilled in the art are intended to be within the scope and nature of the invention which are defined in the appended claims.

What is claimed is:

1. A process for the preparation of (2S,3S,5S)-5-(N-(N-((N-Methyl-N-((2-isopropyl-4-thiazolyl)methyl)amino)carbonyl)-L-valinyl)amino)-2-(N-((5-thiazolyl)methoxycarbonyl)amino)-1,6-diphenyl-3-hydroxyhexane or an acid addition salt thereof comprising converting a mixed anhydride derivative of N-((N-methyl-N-((2-isopropyl-4-thiazolyl)methyl)amino)carbonyl)-L-valine to an activated ester derivative of N-((N-methyl-N-((2-isopropyl-4-thiazolyl)methyl)amino)carbonyl)-L-valine, followed by reacting the activated ester with (2S,3S,5S)-5-amino-2-(N-((5-thiazolyl) methoxycarbonyl)amino)-1,6-diphenyl-3-hydroxyhexane.

2. The process of claim 1 comprising converting a compound of the formula:

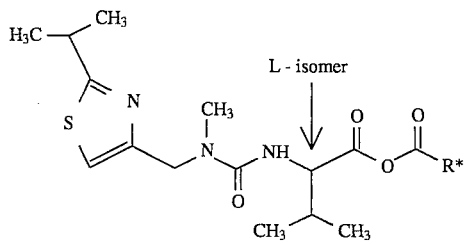

wherein R* is loweralkyl or alkoxy to an activated ester derivative of N-((N-methyl-N-((2-isopropyl-4-thiazolyl)methyl)amino)carbonyl)-L-valine, followed by reacting the activated ester with (2S,3S,5S)-5-amino-2-(N-((5-thiazolyl) methoxycarbonyl)amino)-1,6-diphenyl-3-hydroxyhexane.

3. The process of claim 1 comprising reacting a compound of the formula:

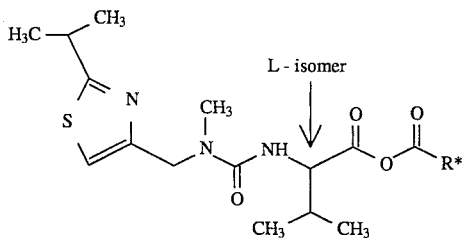

wherein R* is loweralkyl or alkoxy with ROH wherein R is selected from the group consisting of succinimid-1-yl, benzotriazol-1-yl, phthalimid-1-yl, 5-norbornene-2,3-dicarboximidyl, quinolin-8-yl, 1,2,3-benzotrazin-4(3H)-on-3-yl, piperidin-1-yl, pentachlorophenyl, 2,4,5-trichlorophenyl, 2-nitrophenyl, 4-nitrophenyl and pentafluorophenyl to provide an activated ester of the formula:

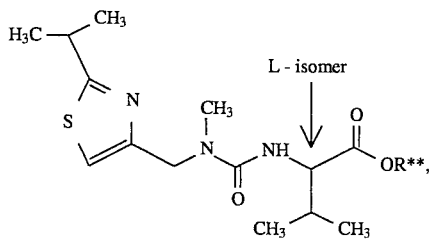

followed by reacting the activated ester with (2S,3S,5S)-5-amino-2-(N-((5-thiazolyl)methoxycarbonyl)amino)-1,6-diphenyl-3-hydroxyhexane.

4. A process for the preparation of (2S,3S,5S)-5-(N-(N-((N-Methyl-N-((2-isopropyl-4-thiazolyl)methyl)amino)carbonyl)-L-valinyl)amino)-2-(N-((5-thiazolyl)methoxycarbonyl)amino)-1,6-diphenyl-3-hydroxyhexane or an acid addition salt thereof comprising reacting a compound of the formula:

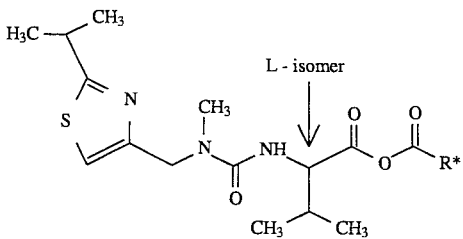

wherein R* is isobutoxy with ROH wherein R is succinimid-1-yl to provide an activated ester of the formula:

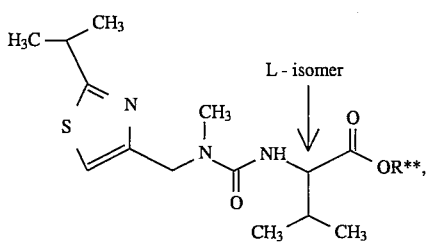

followed by reacting the activated ester with (2S,3S,5S)-5-amino-2-(N-((5-thiazolyl)methoxycarbonyl)amino)-1,6-diphenyl-3-hydroxyhexane.

5. A process for the preparation of (2S,3S,5S)-5-(N-(N-((N-Methyl-N-((2-isopropyl-4-thiazolyl)methyl)amino)carbonyl)-D-valinyl)amino)-2-(N-( (5-thiazolyl)methoxycarbonyl)amino)-1,6-diphenyl-3-hydroxyhexane or an acid addition salt thereof comprising converting a mixed anhydride derivative of N-((N-methyl-N-((2-isopropyl-4-thiazolyl)methyl)amino)carbonyl)-D-valine to an activated ester derivative of N-((N-methyl-N-((2-isopropyl-4-thiazolyl)methyl)amino)carbonyl)-D-valine, followed by reacting the activated ester with (2S,3S,5S)-5-amino-2-(N-((5-thiazolyl)methoxycarbonyl)amino)-1,6-diphenyl-3-hydroxyhexane.

6. The process of claim 5 comprising converting a compound of the formula:

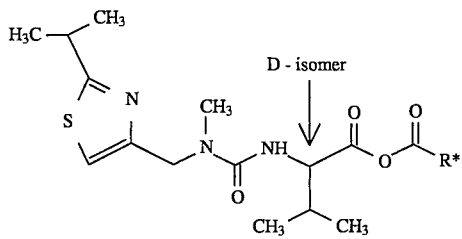

wherein R* is loweralkyl or alkoxy to an activated ester derivative of N-((N-methyl-N-((2-isopropyl-4-thiazolyl)methyl)amino)carbonyl)-D-valine, followed by reacting the activated ester with (2S,3S,5S)-5-amino-2-(N-((5-thiazolyl) methoxycarbonyl)amino)-1,6-diphenyl-3-hydroxyhexane.

7. The process of claim 5 comprising reacting a compound of the formula:

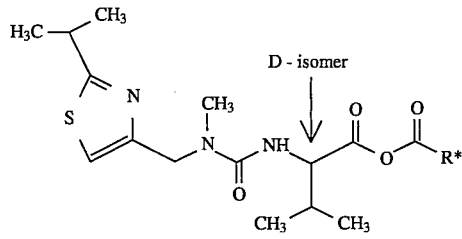

wherein R* is loweralkyl or alkoxy with ROH wherein R is selected from the group consisting of succinimid-1-yl, benzotriazol-1-yl, phthalimid-1-yl, 5-norbornene-2,3-dicarboximidyl, quinolin-8yl, 1,2,3-benzotrazin-4(3H)-on-3-yl, piperidin-1-yl, pentachlorophenyl, 2,4,5-trichlorophenyl, 2-nitrophenyl, 4-nitrophenyl and pentafluorophenyl to provide an activated ester of the formula:

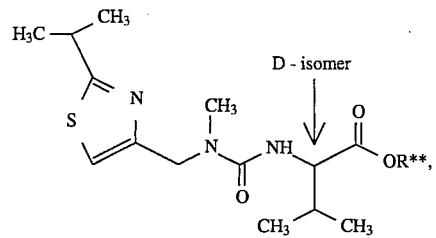

followed by reacting the activated ester with (2S,3S,5S)-5-amino-2-(N-((5-thiazolyl)methoxycarbonyl)amino)-1,6-diphenyl-3-hydroxyhexane.

8. A process for the preparation of (2S,3S,5S)-5-(N-(N-((N-Methyl-N-((2-isopropyl-4-thiazolyl)methyl)amino)carbonyl)-D-valinyl)amino)-2-(N-( (5-thiazolyl)methoxycarbonyl)amino)-1,6-diphenyl-3-hydroxyhexane or an acid addition salt thereof comprising reacting a compound of the formula:

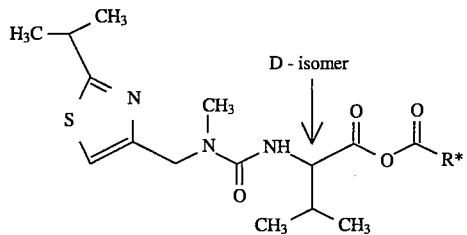

wherein R* is isobutoxy with ROH wherein R is succinimid-1-yl to provide an activated ester of the formula:

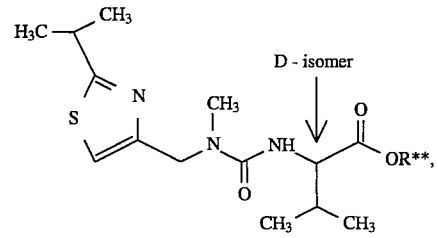

followed by reacting the activated ester with (2S,3S,5S)-5-amino-2-(N-((5-thiazolyl)methoxycarbonyl)amino)- 1,6-diphenyl-3-hydroxyhexane.

* * * * *

UNITED STATES PATENT AND TRADEMARK OFFICE
CERTIFICATE OF CORRECTION

PATENT NO. : 5,567,823
DATED : Oct. 22, 1996
INVENTOR(S) : Tien et al.

It is certified that error appears in the above-indentified patent and that said Letters Patent is hereby corrected as shown below:

Column 7, line 13, insert "-"before "2".

Signed and Sealed this

Eighteenth Day of November 1997

BRUCE LEHMAN

Attest:

Attesting Officer

Commissioner of Patents and Trademarks